(12) United States Patent
Dreier et al.

(10) Patent No.: US 7,809,447 B2
(45) Date of Patent: Oct. 5, 2010

(54) IMPLANTABLE MEDICAL ELECTRODE DEVICE, IN PARTICULAR CARDIOVASCULAR CARDIAC PACEMAKER OR DEFIBRILLATOR ELECTRODE DEVICE

(75) Inventors: Eckard Dreier, Berlin (DE); Erhard Flach, Berlin (DE); Wolfgang Geistert, Rheinfelden (DE); Michelle Maxfield, Berlin (DE); Jochen Palm, Mahlow (DE); Marc Schurr, Berlin (DE); Jan-Heiner Brinkmann, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 260 days.

(21) Appl. No.: 11/683,900

(22) Filed: Mar. 8, 2007

(65) Prior Publication Data

US 2007/0213798 A1  Sep. 13, 2007

(30) Foreign Application Priority Data

Mar. 11, 2006  (DE) .................. 10 2006 011 349

(51) Int. Cl.
*A61N 1/00* (2006.01)
(52) U.S. Cl. ...................... 607/126; 607/128
(58) Field of Classification Search .......... 607/115, 607/116, 119, 122, 126, 127, 128, 130
See application file for complete search history.

(56) References Cited

U.S. PATENT DOCUMENTS

| 3,937,225 A | 2/1976 | Schramm |
| 4,913,164 A | 4/1990 | Green |
| 5,170,802 A | 12/1992 | Mehra |
| 5,411,546 A | 5/1995 | Bowald et al. |
| 5,871,483 A * | 2/1999 | Jackson et al. ............. 606/41 |
| 5,954,761 A | 9/1999 | Machek |
| 6,529,779 B1 | 3/2003 | Sutton |
| 6,805,707 B1 * | 10/2004 | Hong et al. ............. 623/1.16 |
| 2006/0036307 A1 | 2/2006 | Zarembo |

FOREIGN PATENT DOCUMENTS

| DE | 3718139 C1 | 12/1988 |
| EP | 0546414 A1 | 6/1993 |
| EP | 0779080 A1 | 6/1997 |
| EP | 0261582 A1 | 3/1998 |
| EP | 1062972 A | 12/2000 |
| WO | WO 94/07564 | 4/1994 |
| WO | WO 98/42403 A1 | 10/1998 |

OTHER PUBLICATIONS

German Search Report, dated Nov. 13, 2006.
European Search Report, dated Jun. 1, 2007.
European Search Report, dated Sep. 24, 2007.

* cited by examiner

*Primary Examiner*—Mark W Bockelman
*Assistant Examiner*—Elizabeth K So
(74) *Attorney, Agent, or Firm*—ARC IP Law, PC; Joseph J. Mayo

(57) ABSTRACT

An implantable medical electrode device, in particular a cardiovascular cardiac pacemaker or defibrillator electrode device, comprises an elongate, tubular electrode body (2), a fixing zone (4) in front of the distal end (3) of the electrode body (2), in which the externally closed peripheral envelope (8) of the electrode body (2) is reversibly expandable into a body lumen (27) for detachable fixing of the electrode device (1), and an expansion apparatus, situated in the fixing zone (4), for controlling the expansion and contraction in the fixing zone (4).

3 Claims, 7 Drawing Sheets

IMPLANTABLE MEDICAL ELECTRODE DEVICE, IN PARTICULAR CARDIOVASCULAR CARDIAC PACEMAKER OR DEFIBRILLATOR ELECTRODE DEVICE

This application takes priority from German Patent Application DE 10 2006 011 349.7 filed 11 Mar. 2006, the specification of which is hereby incorporated herein by reference.

BACKGROUND OF THE INVENTION

1. Field of the Invention

The present invention relates to an implantable medical electrode device and, in particular, a cardiovascular cardiac pacemaker or defibrillator electrode device.

2. Description of the Related Art

On the background of the present invention, it is to be noted that implantable electrode devices of this type must be anchored at a specific body location, so that they do not change their position over the course of time. This is especially important when such electrode devices are implanted in a moving organ, such as the heart.

To fix the electrode device, implementing fixing units, such as screws, needles, hooks, anchors (tines), or projections and corresponding undercuts, into which the tissue may grow, on their elongate, tubular electrode bodies in a fixing zone before the distal end is known.

Fixing in a blood vessel represents a special case, since sharp tips or edges of the fixing units may cause injuries or at least irritations on the vessel wall here in particular. For this reason, typical fixing units are designed in such a way that they jam in the vessel because of their shaping.

In addition to the anchoring of such electrode devices, which is as atraumatic as possible, fixing in vessels of various diameters also plays a role.

Electrode devices implantable in vessels, which have the above-mentioned "tines", silicone screws, or helical and/or hooked electrode bodies, are commercially available. Through pre-shaped electrode bodies of this type, for example, having bending points applied in a targeted way, the electrode body may be applied in a formfitting way to the angles and discharges of veins in the cardiovascular system, for example, and thus achieve fixing. In linear veins, positional fixing may be performed by stretching these targeted bends. Furthermore, electrodes which have an electrode body shaped as a helix on the distal end, which clamps on the vascular wall by expansion forces, are known.

An especially simple fixing technology, which does not achieve optimal therapeutic results, however, is wedging the distal tip of the electrode body in the vessel. The electrode body is advanced into the left-ventricular vein branch, for example, until the tip of the electrode body jams in the vein and assumes a "wedge position". The vein is closed in this position.

All of the preceding anchoring technologies have various disadvantages, such as the dependence of the final position of the electrode body on the ratio the diameter of the vein to the dimensions of the tip, helix anchors, or "tines". The final position of the electrode body thus achievable is not necessarily the most favorable therapeutic position.

Reference is made to, for example, WO 98/42403 A1 or U.S. Pat. No. 5,170,802 A of the published prior art. These publications disclose a fixing unit having a "stent", which is expanded when the electrode device is located at the desired position in the vessel. The electrode body is wedged in position by the expansion of the stent structure. This solution has the disadvantage that the fixing is not reversible, which make detaching and replacing the electrode device after a first fixing, which is sometimes necessary, and also removal of the electrode device difficult.

A solution for the problem of repositioning is disclosed in WO 94/07564 A1, in which the fixing is performed by an expandable or self-expanding wire basket. This construction has the disadvantage that the wires cut into the vascular wall and thus may be very traumatic.

Finally, U.S. Pat. No. 5,411,546 A1 discloses various solutions for fixing in a vessel, for example, wire spirals which are reversibly extendable from the catheter envelope and retractable back therein. However, the fixing is not very reliable, due to the smaller diameter of the wires and the small contact area between spirals and vascular wall connected thereto, and the limited clamping force with which the spirals may press against the vascular wall, so that the latter is not damaged. The wire constructions also disclosed in the publication are—as already mentioned above—highly traumatic. Furthermore, a "sail construction" is also disclosed in this published prior art, which is again not reversible.

BRIEF SUMMARY OF THE INVENTION

Proceeding therefrom, the present invention is based on the object of providing an electrode device, which allows reliable but also reversible fixing and is comparatively atraumatic.

This object is achieved according to the present invention by the features of the electrode device specified in Claim 1, according to which the electrode body is provided in the area of its fixing zone with an externally closed peripheral envelope, which is reversibly expandable for removable fixing in a body lumen, however. Expansion means are provided for controlling the expansion in the fixing zone, which may be implemented in greatly varying ways. It is to be noted on the externally closed peripheral envelope that it may be the wall of the actual electrode body of the electrode device, or also separate tubing drawn over the electrode body.

Because of the preceding construction of the fixing zone according to the present invention, secure, atraumatic fixing of the electrode device in a vein in the heart is possible, for example, by expanding the peripheral envelope by the expansion means (such as fluid pressure, a balloon, or axial tension/pressure on the fixing zone) at the desired position until the peripheral envelope is fixed in the vessel. It may be seen that fixing is performed independently of the diameter of the body lumen—of course, within certain boundaries. Because an externally closed envelope expands, no sharp wires, corners, or edges project into the fixing zone, so that the fixing—as provided according to the object—is performed very atraumatically.

Preferred embodiments of the expandable fixing zone having alternative expansion means are specified in the subclaims. To avoid repetitions, reference is made to the following description for more detailed discussion thereof, in which various exemplary embodiments of the subject matter of the present invention are explained on the basis of the attached drawings.

DETAILED DESCRIPTION

Figure 1:
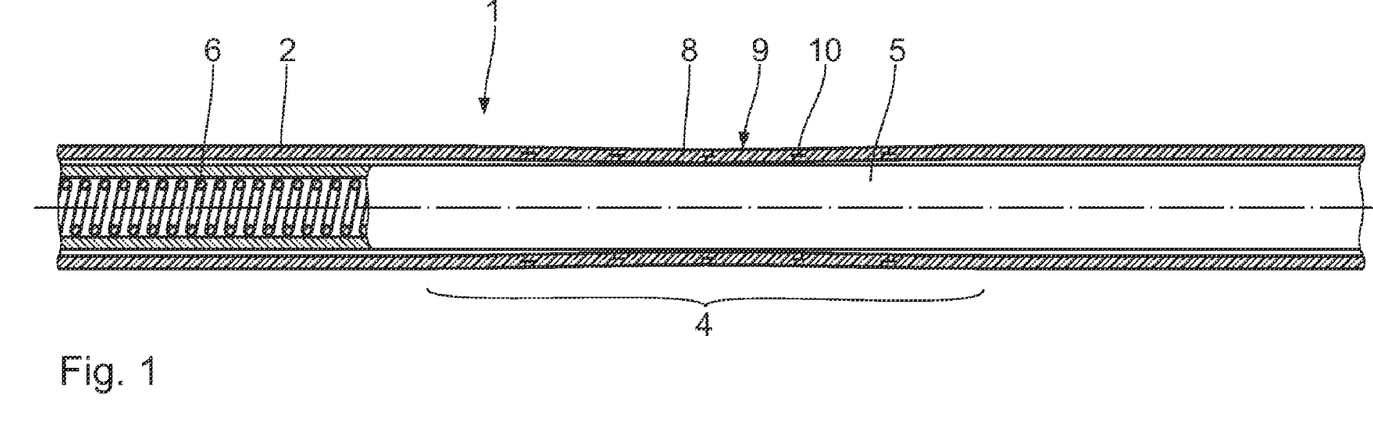
FIGS. 1 and 2 show a longitudinal section through the fixing zone of an electrode device in the contracted and expanded states, respectively, of the fixing zone.
Figure 2:
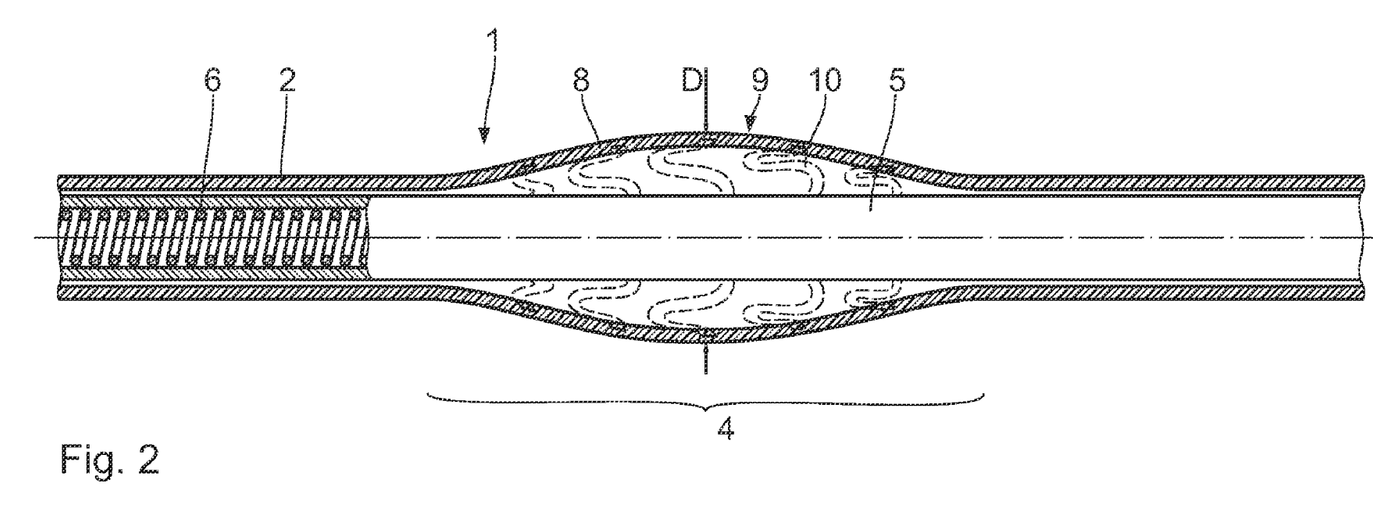

As is clear from FIGS. 1 and 2, an implantable medical electrode device in the form of a cardiac catheter, identified as a whole by 1, has an elongate, tubular electrode body 2, which is provided in front of the distal end 3 (FIG. 3) with a fixing zone 4, which is a few millimeters long. The coiled electrode supply lines 6, using which the stimulation electrodes 7 shown in FIG. 3 are supplied with voltage, for example, run in separate internal tubing 5 in the interior of the electrode body 2.

The wall 8 of the electrode body 2 is implemented as more flexible in the area of the fixing zone 4 than in the adjoining remaining areas. Furthermore, a stent-like, plastically deformable support structure 9 is embedded in the wall material therein. This support structure 9 is an essentially tubular, plastically deformable, expandable stretched metal or plastic molded part. The expansion forces of this support structure 9 are to be tailored by suitable material selection and texturing of the ribs 10—for example, by tailoring of the rib width, rib height, the shape of the bending legs, etc.—to the elastic and geometric properties of the embedding material of the wall 8 of the fixing zone 4, which are in turn determined by the wall thickness and the material selection, such as latex, silicone, or polyurethane.

Figure 3:
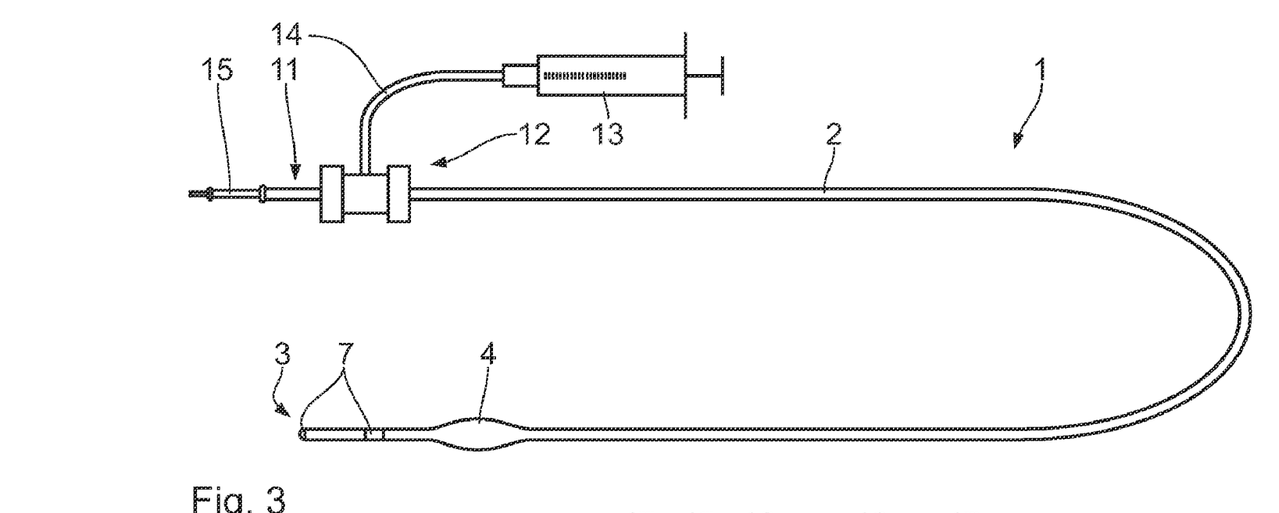
FIG. 3 shows a schematic overall view of an electrode device.

As is clear from FIG. 3, a supply unit 12 is provided around the electrode body 2 at the proximal end 11 of the cardiac catheter 1, via which a hydraulic pressure medium, such as physiological saline solution, may be injected into the electrode body 2, implemented as pressure-tight tubing, at a pressure pH, using a syringe 13 via the attached feed line 14. The proximal end 11 of the cardiac catheter 1 is formed by a terminal plug 15 for the individual stimulation electrodes 7.

Figure 4:
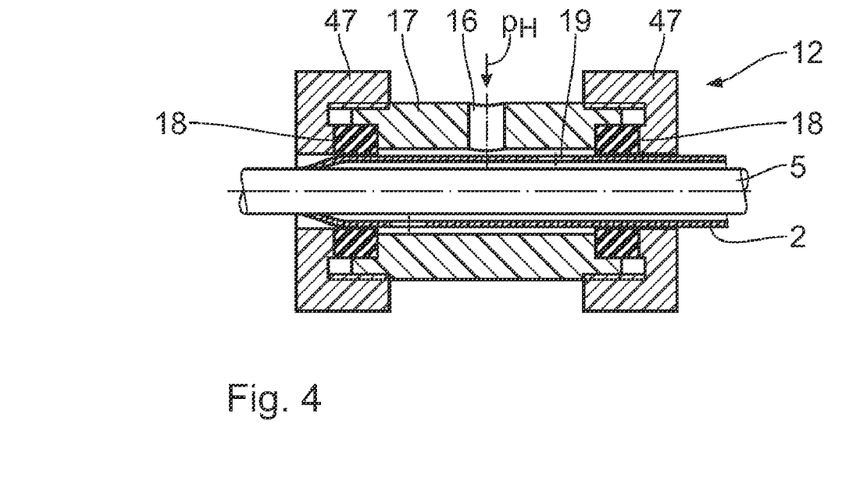
FIG. 4 shows a detail axial section of the electrode device in the area of the proximal pressure medium supply.

The supply unit 12 is illustrated in FIG. 4. The connection 16 of the feed line 14 is seated centrally in wall of a cylindrical sleeve 17 enclosing one of the electrode bodies 2, between whose front openings and the electrode body 2, O-ring seals 18 are fitted in each case. These seals are impinged by clamping sleeves 47 which may be screwed onto the cylindrical sleeve 17 for the seal, so that the pressure fluid may be injected into the annular space between the electrode body 2 and the internal tubing 5 via the connection 16 and a feed opening 19.

As is clear from FIGS. 1 and 2, the distal end 3 of the cardiac catheter 1 is advanced in the coronary sinus until the desired position of the stimulation electrodes 7 is reached, for example. The ability to monitor this procedure using x-rays is improvable by an appropriate design of the support structure 9 from an x-ray-visible material, such as suitably coated plastic, stainless steel, platinum or titanium alloys, magnesium, or gold.

By impinging the fixing zone 4 using the pressure fluid as expansion means, the support structure 9 is plastically expanded there and thus stretches radially outward, as is recognizable in FIG. 2. This is continued until the expanded diameter of the fixing zone 4 presses against the vascular inner wall (not shown here) and thus fixes the cardiac catheter 1 in this position.

For repositioning or removal of the cardiac catheter 1, the pressure fluid is suctioned off, through which a partial vacuum arises, which ensures that the fixing zone 4 contracts again and the support structure 9 more or less collapses, through which the configuration shown in FIG. 1 is achieved again and the cardiac catheter 1 is freely displaceable.

The expansion diameter D in the fixing zone 4 may be directly influenced by control of the introduced volume of the pressure fluid or by the applied pressure—even in the event of pneumatic control. The pressure fluid may also be transferred into the electrode body 2 through an eccentric auxiliary lumen or external, coaxially situated tubing (not shown in detail in the figures).

Finally, it is to be noted that axial deformability is also achievable by suitable shaping of the embedded support structure 9, so that the cardiac catheter 1 also remains sufficiently flexible for placement in the vessels in the area of the fixing zone 4.

Figure 5:
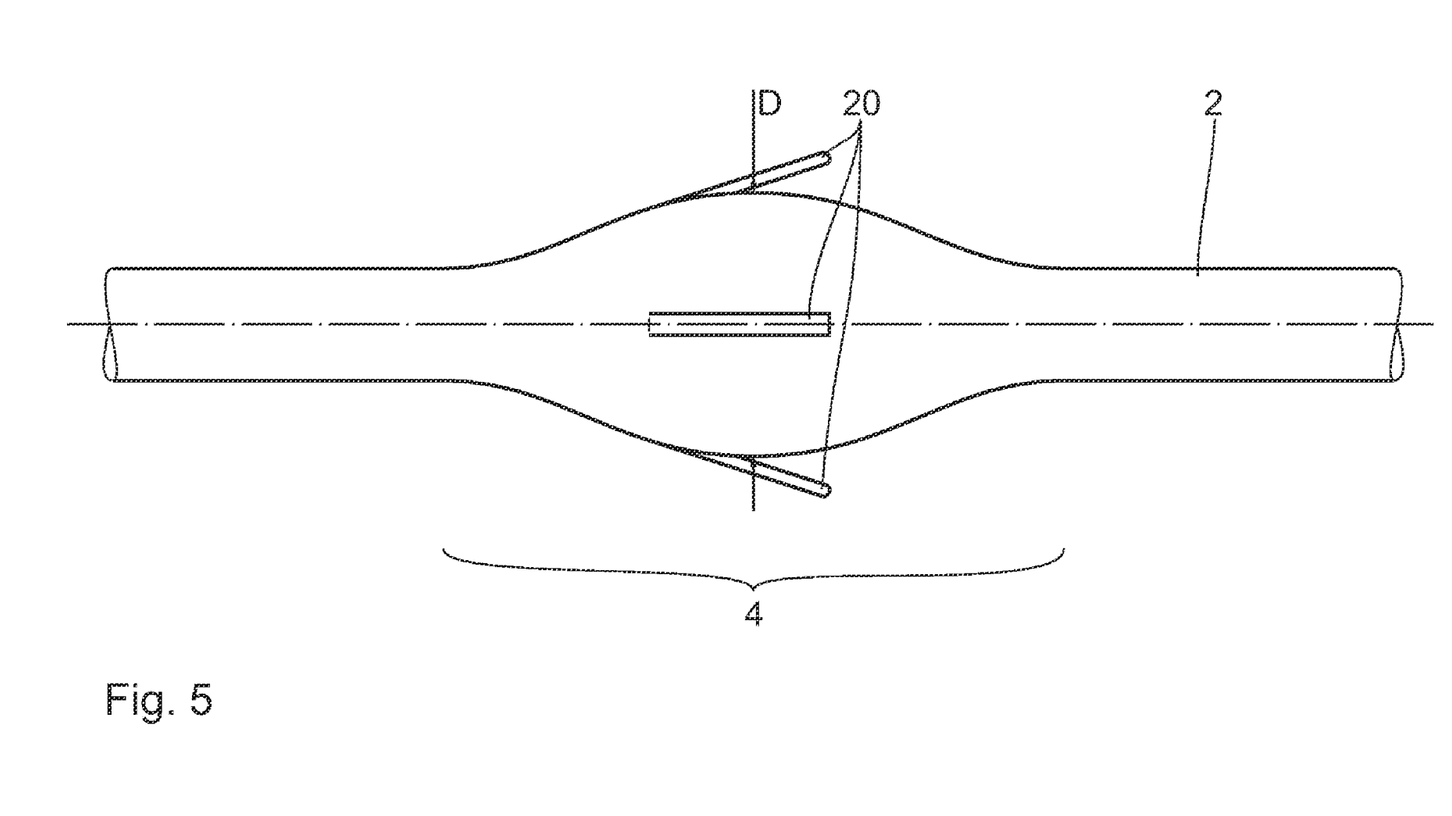
FIG. 5 shows a partial side view of the fixing zone of an electrode body having anchoring elements on the exterior.

As is clear from FIG. 5, additional fixing of the cardiac catheter 1 may be achieved by suitable texturing of the external surface of the fixing zone 4. For this purpose, in a further embodiment, rib-shaped anchoring elements 20 are applied to the exterior distributed around the circumference parallel to the longitudinal direction of the electrode body 2 in the area of the fixing zone 4. In the unexpanded configuration, these anchoring elements 20 press flat against the exterior of the cardiac catheter 1, so that insertion without problems is ensured. The anchoring elements 20 spread out due to the expansion of the fixing zone 4, as shown in FIG. 5, and additionally mechanically impinge the inner wall of the vessel (not shown here). In particular, significantly greater withdrawal security of the cardiac catheter 1 is thus achieved. The anchoring elements 20 may be designed as soft or rigid depending on the material selection. Elastomers, other plastics, or metals come into consideration as materials.

The exemplary embodiments of the cardiac catheter 1 shown in FIGS. 6 through 19 are based on a purely mechanical control principle. For this purpose, the fixing zone 4 is provided with a folded configuration identified as a whole by 21, which acts as expansion means together with a traction or shear impingement applied coaxially to the electrode body, and is explained in the following in greater detail on the basis of the individual figures.

Figure 6:
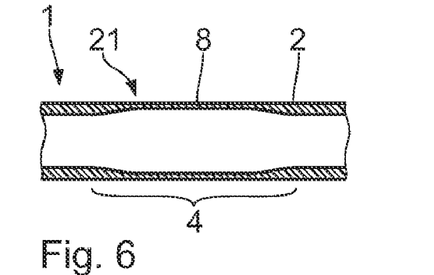
FIG. 6 through 19 show schematic detailed longitudinal axial sections of the fixing zone of electrode devices having a folded configuration in various embodiments.
Figure 7:
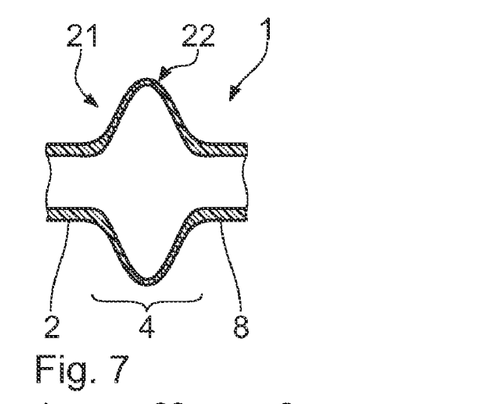

Thus, FIG. 6 shows a reduction of the wall thickness of the electrode body 2 in the area of the fixing zone 4. If, after positioning of the cardiac catheter 1, a pull wire (not shown in greater detail), which is attached to the tip of the electrode body 2, has traction applied to it in the proximal direction in relation to the electrode body 2, the electrode body 2 bulges out in the area of the thin part of the wall and forms an annular fold 22 projecting radially outward (FIG. 7). This fold is crowned in cross-section and thus atraumatic. The diameter of the annular fold 22 is expanded until the latter presses securely against a vascular wall and provides anchoring of the cardiac catheter 1.

Figure 8:
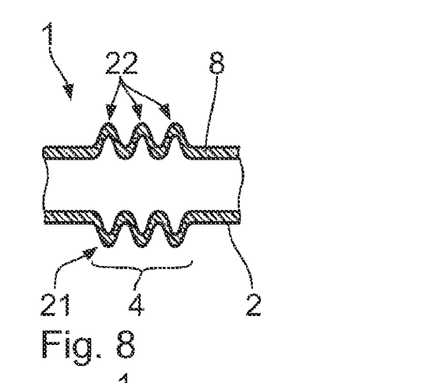

An exemplary embodiment is shown in FIG. 8, in which three annular folds 22 arrayed in the axial direction arise upon traction impingement of the pull wire due to three narrower thin parts of the wall arrayed in the axial direction.

Figure 9:
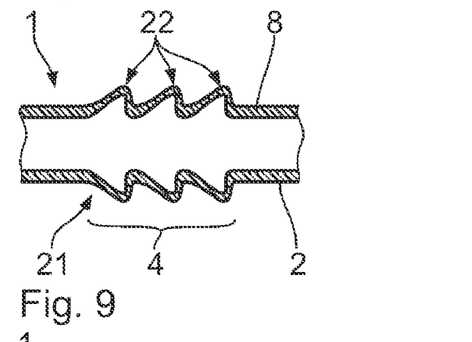

For a corresponding design of the wall 8 in diameter and/or varying flexibility of the wall material, the annular fold 22 may also form a sawtooth profile after the expansion, as shown in FIG. 9. The retention force is thus greater in the withdrawal direction of the cardiac catheter 1 than in the insertion direction.

Figure 10:
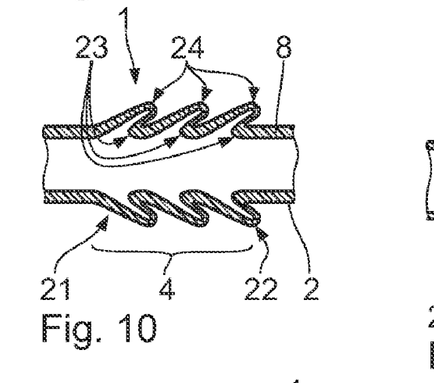

In the embodiment shown in FIG. 10, the wall 8 is designed in such a way that upon expansion with the aid of the pull wire (not shown), the annular folds 22 slide one over another, so that multiple centrally positioned internal folds 23 and multiple peripherally positioned external folds 24 arise. Therefore, the diameter expansion of the electrode body 2 is not only based solely on folding, but rather also on thickening of the material by forming multiple, preferably at least three layers.

Figure 11:
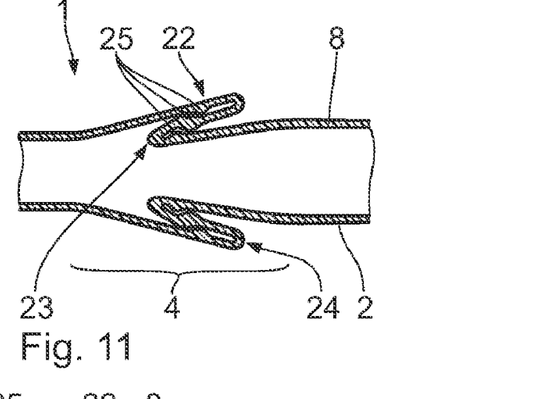
Figure 12:
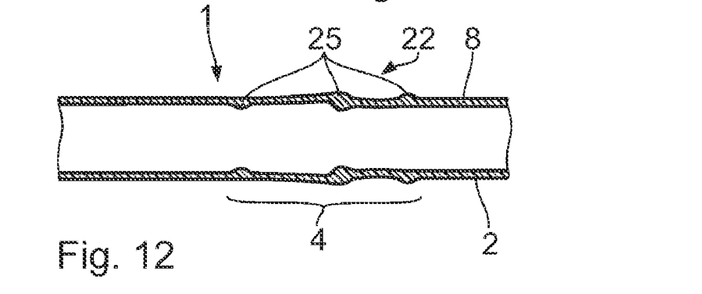

FIGS. 11 and 12 shows an embodiment in which a single annular fold 22 is formed, the thick parts 25 introduced in the wall 8 sliding one over another in layers in such a way that the layers are locked. If the internal fold 23 is pushed under the external fold 24 as the folds are pushed together, the thick part 25 of the internal fold 23 snaps behind the corresponding thick part 25 of the external fold 24, by which the configuration formed is fixed.

Figure 13:
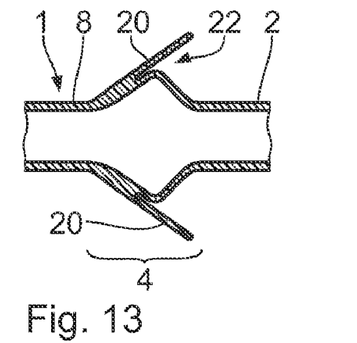
Figure 14:
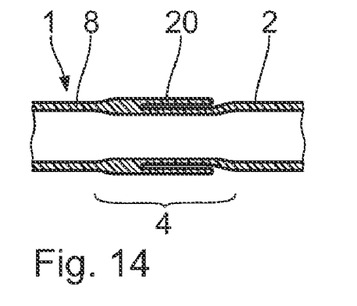

In the embodiment shown in FIG. 13, rib-like anchoring elements 20 are again provided around the circumference at the edge of the fixing zone 4, which are spread out upon expansion of the annular folds 22 and additionally anchor themselves in the vascular wall. FIG. 14 shows the corresponding area of the cardiac catheter 1 in the stretched state, in which the anchoring elements 20 press against the stretched electrode body 2.

Figure 15:
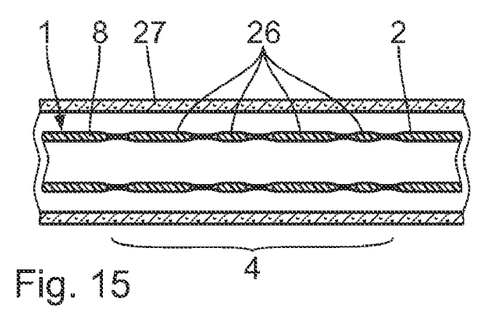
Figure 16:
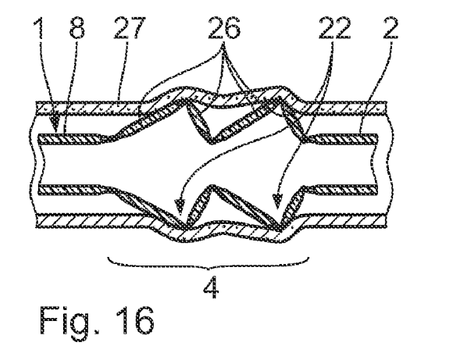
Figure 17:
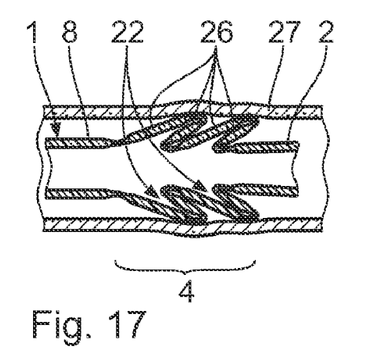

In the embodiment shown in FIG. 15, the electrode body 2 is designed in regard to its material selection and wall diameter in the fixing zone 4 in such a way that the flanks 26 of the annular folds 22 forming are stiffened. If the cardiac catheter 1, as shown in this figure, is positioned in the vessel 27, the pull wire (not shown) is actuated and the folding occurs, as shown in FIG. 16 in an intermediate state. In this state, the vessel 27 is somewhat overexpanded. Upon further actuation of the pull wire, the annular folds 22 fold over the radially maximally expanded configuration again, so that the stiffened flanks 26 lie one on top of another and fix the cardiac catheter 1 in the vessel 27 (FIG. 17).

Figure 18:
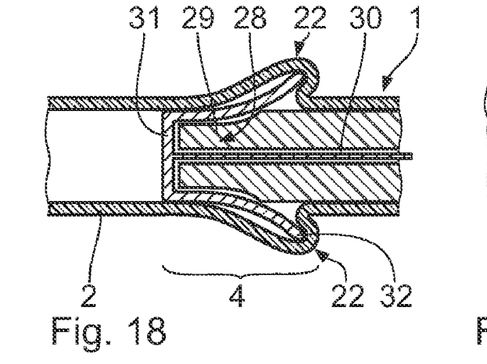
Figure 19:
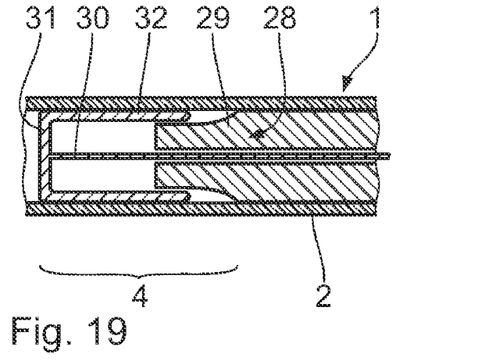
Figure 20:
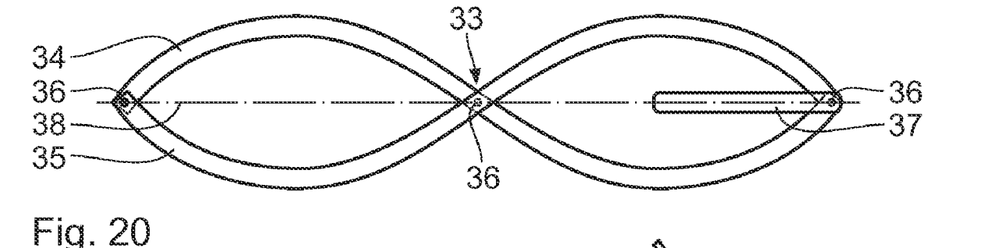
FIG. 20 shows a top view of a bistable tilting element for use in the fixing zone of an electrode body.

In the variation shown in FIGS. 18 and 19, a spreading unit 28, which supports the folding, is provided in the electrode body 2 in the area of the fixing zone 4. This spreading unit 28 has a cone 29 fixed in the electrode body 2, which cooperates with a spreading sleeve 31, which is mounted distally in front of it and is impinged by the pull wire 30. Upon impingement of the pull wire 30 in the proximal direction, the cone 29 engages under the spreading arms 32 of the spreading sleeve 31, which thus radially expand and contribute to the formation of the annular folds 22. The stability of the fixing may be increased by the spreading unit 28. With an elastic embodiment of the spreading arms 32—and also the anchoring elements 20—the folding and opening out of the anchoring elements 20 are reversible. As already noted, the folding may be optimized both by variation of the wall thickness of the electrode body 2 in the fixing zone 4 and also by varying the degrees of hardness of the material and/or by pre-shaping using memory effect.

As is not shown in detail in FIGS. 6 through 19, the distal end of the fixing zone 4 may be connected to a pull wire or pull cable, which runs inside the electrode body 2 and is situated so it is movable in relation thereto. The proximal end of the pull wire extends beyond the proximal end of the electrode body 2. Pulling on the pull wire or fixing the pull wire while simultaneously advancing the electrode body 2 allows the distal and the proximal ends of the fixing zone 4 to move toward one another, which causes the annular folds 22 to bulge outward, possibly with formation of the internal and external folds 23, 24. It is possible to disengage the fixing of the cardiac catheter 1 thus performed by pushing on the pull wire, if it is sufficiently stiff. As an alternative, a stylet may be inserted into the electrode body 2, using which the distal end of the flexible area may be pushed forward again. In a kinematic reversal, the pull wire having the distal end may also be used as a buttress, if the proximal end of the electrode body 2 is retracted. In any case, contraction and smoothing of the folds and stretching of the fixing zone 4 while releasing the cardiac catheter 1 will occur.

Finally, a further variation of the expansion and contraction of the cardiac catheter 1 in the area of its fixing zone 4 is illustrated in FIGS. 20 through 24. This is based on the bistable tilting element 33 shown in a top view in FIG. 20, which comprises two legs 34, 35, each bent in an S-shape. These are laid mirror-reversed on one another and riveted to one another at the intersection points 36. Furthermore, an anchoring element 37 in the form of a sheet metal lamella is again attached at one terminal intersection point 36, which projects inward in the direction of the main axis connecting the intersection points 36. The two legs 34, 35 form the shape of an 8 in a top view—as may be seen well in FIG. 20.

Figure 21:
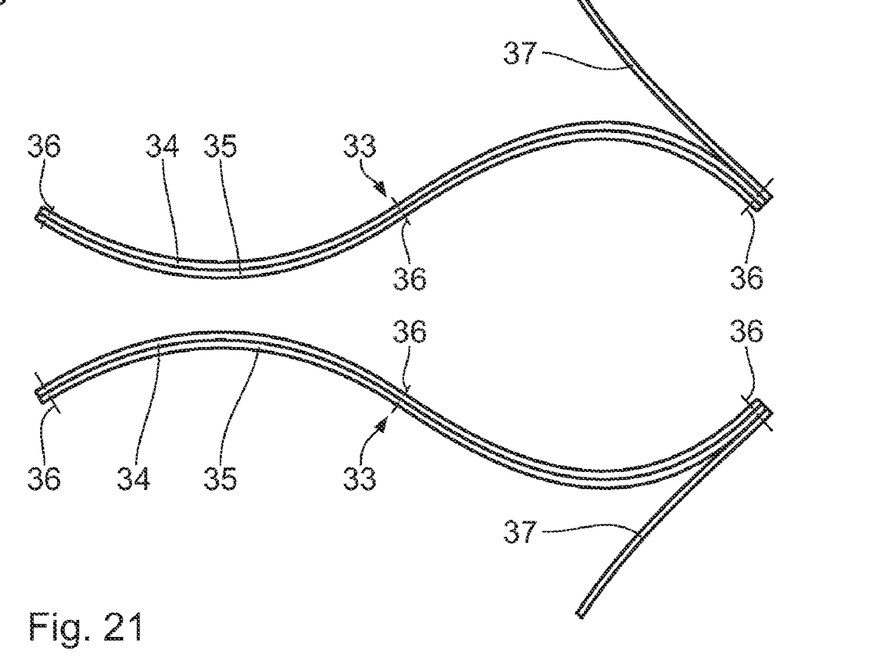
FIGS. 21 and 22 show schematic side views of two such tilting elements in the expanded and contracted states of the fixing zone, respectively.
Figure 22:
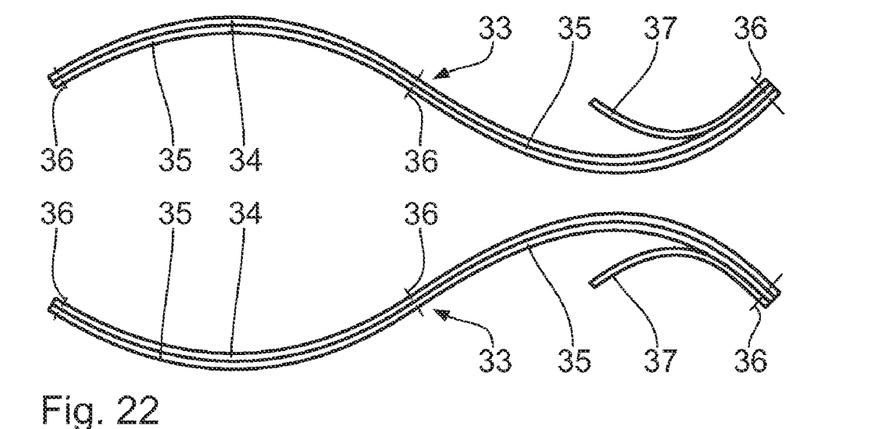

As may be seen from FIGS. 21 and 22, the legs 34, 35 are not planar in a side view, but rather are connected to one another under tension by riveting in such a way that the tilting element 33 is also bent in an S-shape along its longitudinal axis 38. FIG. 21 shows two such tilting elements 33 in a configuration which corresponds to the application shown in FIGS. 23 and 24 in the expanded state. The sections of the legs 34, 35 supporting the anchoring elements 37 are bent convex, the remaining sections are bent concave. This is a stable final position, which may be snapped over into the second stable final position illustrated in FIG. 22 by impinging the concave sections of the legs 34, 35 outward. In this position, the sections of the legs 34, 35 supporting the anchoring elements 37 are bent concave, while the remaining sections are now convex. Overall, the tilting element 33 may thus be snapped over between a concave-convex and a convex-concave configuration to pass between the expanded and the contracted states.

Figure 23:
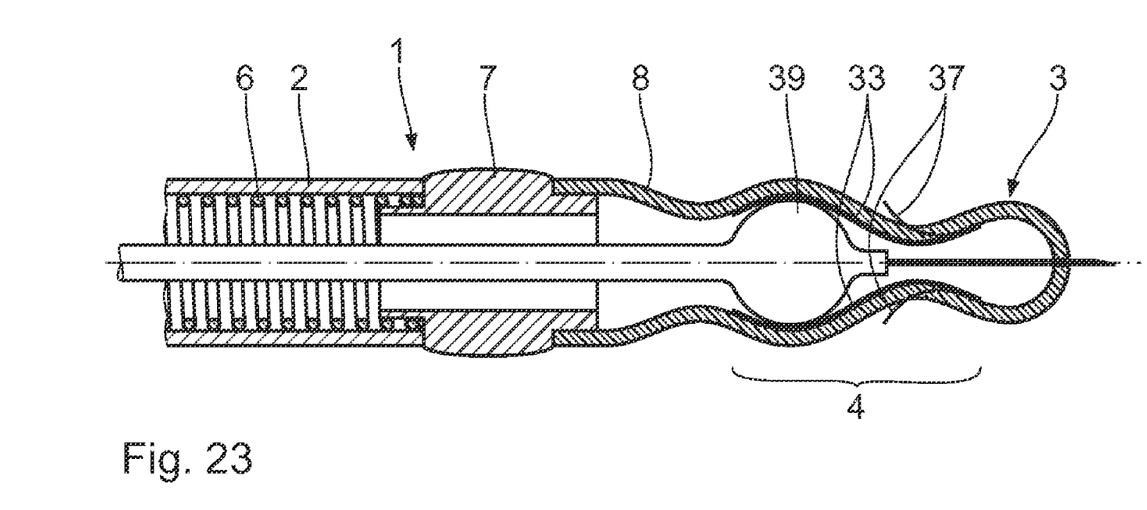
FIGS. 23 and 24 show detail longitudinal axial sections through the fixing zone of an electrode body which has the tilting elements from FIGS. 20 through 22.
Figure 24:
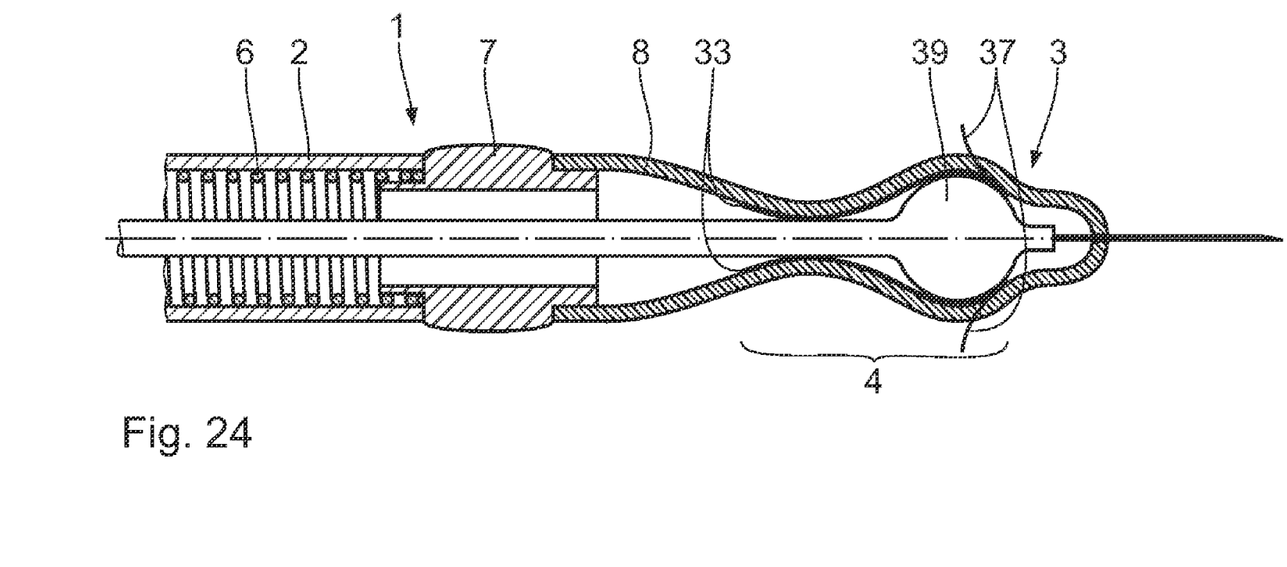

As shown in FIGS. 23 and 24, the legs 34, 35 of the tilting element 33 are completely embedded in the wall 8 of the electrode body 2, so that the latter again forms an externally closed envelope. Only the anchoring elements 37 project outward from the wall 8.

To implant a corresponding cardiac catheter 1, the embedded tilting elements 33, as shown in FIG. 23, are brought into the bistable final position in which the anchoring elements 37 are retracted by concave shaping of the corresponding sections of the legs 34, 35. Subsequently, a deflated catheter balloon 39 is drawn through the electrode body 2 up to below this concave section and inflated as expansion means. The corresponding sections of the legs 34, 35 are thus arched outward, the tilting elements 33 thus jump over into the other bistable final position shown in FIG. 24, in which the anchoring elements 37 project outward due to the convex shape of the sections of the legs 34, 35 on which they are mounted and ensure reliable anchoring of the cardiac catheter 1 in the vessel (not shown).

To achieve this anchoring, it is sufficient to position a deflated balloon 39 between the concavely arched sections of the legs 34, 35 and reinflate the balloon 39, as shown in FIG. 23. The tilting elements 33 thus jump back into the other bistable final position, which is shown in FIG. 23. The cardiac catheter 1 may then be withdrawn or repositioned without problems.

What is claimed is:

1. An implantable medical electrode device, or a cardiovascular cardiac pacemaker or defibrillator electrode device, comprising:
an electrode body (2) that is elongate and tubular;
an externally closed peripheral wall (8) coupled with said electrode body (2);
a fixing zone (4) in front of a distal end (3) of said electrode body (2), wherein said fixing zone (4) is configured to be reversibly expandable and is configured to detachably fix an electrode device (1) in a body lumen;
expansion means situated in said fixing zone (4) and configured to control expansion and contraction in said fixing zone (4);
wherein said fixing zone (4) is configured to snap into a stationary expanded fixing state through application of force at a first location of said electrode body (2) and is configured to snap into a contracted starting state through application of force at a second location of said electrode body (2); and,
wherein said peripheral wall is provided with at least one mechanically expanding, bistable tilting element (33) in said wall in an area of said fixing zone (4), wherein said bistable tilting element (33) comprises two stable positions that define the stationary expanded fixing state and the contracted starting state of said fixing zone (4) and wherein said bistable tilting element (33) is configured to maintain each of said two stable positions without the application of force applied to said bistable tilting element at said first location or said second location of said electrode body (2) when said expansion means is removed from said fixing zone (4).

2. The electrode device according to claim 1, wherein at least one said tilting element (33) is bent in a S-shape along its longitudinal axis (38) oriented parallel to an electrode longitudinal direction and may be snapped over between a concave-convex and a convex-concave configuration, each of which is stable, to transfer it between expanded and contracted states.

3. The electrode device according to claim 1 wherein said tilting element (33) is actuatable as expansion means by a balloon (39) insertable into said electrode body (2).

* * * * *